United States Patent [19]

Bosies et al.

[11] Patent Number: 4,971,958

[45] Date of Patent: Nov. 20, 1990

[54] DIPHOSPHONIC ACID DERIVATIVES, PHARMACEUTICAL COMPOSITIONS AND METHODS

[75] Inventors: Elmar Bosies, Weinheim; Rudi Gall, Hirschberg, both of Fed. Rep. of Germany

[73] Assignee: Boehringer Mannheim GmbH, Mannheim, Fed. Rep. of Germany

[21] Appl. No.: 356,567

[22] Filed: May 23, 1989

Related U.S. Application Data

[63] Continuation of Ser. No. 125,537, Nov. 25, 1987, abandoned.

[30] Foreign Application Priority Data

Nov. 29, 1986 [DE] Fed. Rep. of Germany ....... 3640938

[51] Int. Cl.$^5$ ................ A61K 31/445; A61K 31/495; C07F 9/06; C07F 9/08
[52] U.S. Cl. .......................................... 514/89; 514/91; 514/80; 514/81; 514/82; 514/85; 514/86; 514/87; 514/88; 514/94; 544/232; 548/112; 548/113; 548/413; 548/414; 546/22
[58] Field of Search .............................. 546/22; 514/89

[56] References Cited

U.S. PATENT DOCUMENTS 3,988,443 10/1976 Plöger et al. ................ 514/89
4,761,406 8/1988 Flora et al. ................... 514/89

FOREIGN PATENT DOCUMENTS

| 0001584 | 5/1979 | European Pat. Off. | 546/22 |
| 0170228 | 2/1986 | European Pat. Off. | 546/22 |
| 0186405 | 7/1986 | European Pat. Off. | 546/22 |
| 0258618 | 3/1988 | European Pat. Off. | 546/22 |
| 0272208 | 6/1988 | European Pat. Off. | 546/22 |
| 0274158 | 7/1988 | European Pat. Off. | 546/22 |
| 0275821 | 7/1988 | European Pat. Off. | 546/22 |
| 1958123 | 5/1971 | Fed. Rep. of Germany | 546/22 |
| 0059674 | 5/1978 | Japan | 546/22 |

OTHER PUBLICATIONS

Chemical Abstracts, 74-Radiation Chem., Photochem., vol. 96, 1982, p. 591. 774832.
Chemical Abstracts, 1-Pharmacology, vol. 99, 1983, p. 640.

*Primary Examiner*—John M. Ford
*Assistant Examiner*—J. Richter
*Attorney, Agent, or Firm*—Felfe & Lynch

[57] ABSTRACT

The present invention provides diphosphonic acid derivatives of the general formula:

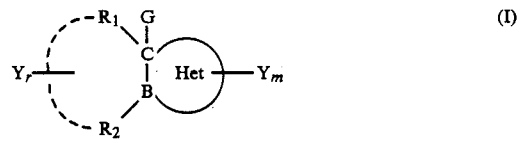

(I)

according to claim 1. These compounds are useful for the treatment or prophylaxis of calcium metabolism disturbance or disease.

14 Claims, No Drawings

DIPHOSPHONIC ACID DERIVATIVES, PHARMACEUTICAL COMPOSITIONS AND METHODS

This application is a continuation of application Ser. No. 125,537, filed Nov. 25, 1987, now abandoned.

The present invention is concerned with new diphosphonic acid derivatives and processes for their preparation, as well as with pharmaceutical compositions which contain these compounds.

In Federal Republic of Germany Patent Specification No. 18 13 659 are described diphosphonic acid derivatives of which 1-hydroxyethane-1,1-diphosphonic acid has achieved importance as an agent for the treatment of Paget's disease. In Federal Republic of Germany Patent Specification No. 27 45 083 is described, inter alia, 1-hydroxy-1-(pyrrolidin-2-yl)-methane-1,1-diphosphonate as a complex former. In Japanese Kokai Tokkyo Koho 8098.193 are described, inter alia, pyridylmethane-diphosphonates as herbicides and in Federal Republic of Germany Patent Specification No. 34 28 524 are described heteroaromatic alkyl diphosphonates.

We have now found that analogous derivatives of these compounds, in which the heterocycle is completely or partly hydrogenated, also show this action and, furthermore, can be used as good calcium complex formers for the broader treatment of calcium metabolism disturbances. In particular, they can be well used in cases where bone formation and breakdown is disturbed, i.e. they can be used for the treatment of diseases of the skeletal system, for example osteoporosis, Paget's disease, Bechterew's disease and the like.

However, on the basis of these properties, they can also be used in the therapy of bone metastases, of urolithiasis and for the prevention of heterotopic ossification. Furthermore, due to their influencing of the calcium metabolism, they also form a basis for the treatment of rheumatoid arthritis, of osteoarthritis and of degenerative arthrosis.

Consequently, the present invention provides diphosphonates of the general formula:

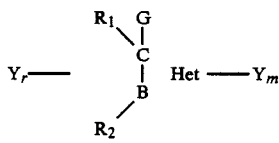

wherein Het is a hydrogenated or partly hydrogenated heterocyclic ring with one or two nitrogen atoms which, independently of one another, can optionally be substituted by lower alkyl, benzyl or cyclohexylmethyl radicals, B is a nitrogen atom or a C-H grouping, whereby the carbon atom substituted by G can also form a double bond with B, $R_1$ and $R_2$ are each hydrogen atoms or lower alkyl radicals or together form an alkylene chain with 3 to 5 carbon atoms, whereby this ring so annelated on Het can contain up to 3 double bonds, Y is a radical of the general formula:

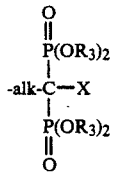

in which $R_3$ is a hydrogen atom or a lower alkyl radical, alk is a valency bond or a straight-chained or branched alkylene chain with 1 to 6 carbon atoms which must not start from a heteroatom, X is a hydrogen atom or a hydroxyl or amino group, G is a hydrogen atom or a radical $Y_s$ and m, r or s can each be 0 or 1, whereby m+r+s must always be 1, with the proviso that, if alk is a valency bond, Het must not be a pyrrolidone ring substituted in the 2-position by Y; as well as the pharmacologically acceptable salts thereof.

The heterocyclic hydrogenated or partly hydrogenated ring is to represent a five-, six- or seven-membered ring, especially a pyrrolidine, pyrroline, pyrazolidine, pyrazoline, piperidine, tetrahydropyridine, hexahydropyrazine, tetrahydropyrazine, tetrahydropyrimidine or hexahydroazepine ring.

Lower alkyl means a hydrocarbon radical with 1 to 4 carbon atoms and preferably a methyl, ethyl or isopropyl radical.

When alk is an alkylene chain, it is preferably methylene, ethylene or propylene.

When $R_1$ and $R_2$, together with the heterocyclic ring, form a bicyclic moiety, they can be one of the following:

dihydroindole, octahydroindole, octahydroisoindole, tetrahydroquinoline, decahydroquinoline, dihydroisoquinoline, tetrahydroisoquinoline, octahydroisoquinoline, decahydroisoquinoline, hexahydrobenzimidazole, dihydroindolizine, octahydroindolizine, dihydroazabicyclo[5,3,0]decane, octahydroaza[5,3,0]decane, octahydropyrindine, dihydropyrrolizine, hexahydropyrrolizine, tetrahydroquinolizine and octahydroquinolizine, but preferably octahydroindole, octahydroisoindole, decahydroquinoline, dihydroisoquinoline, decahydroisoquinoline, dihydroindolizine, octahydroindolizine, octahydropyrindine, dihydropyrrolizine, hexahydropyrrolizine, tetrahydroquinolizine, octahydroquinolizine and tetrahydroquinoxaline.

The alkane-diphosphonic acid group can be not only on the heterocyclic moiety but also on its annelated ring but alkane-diphosphonic acids are preferred which are linked with the heterocyclic moiety.

The compounds can be present as stereoisomeric mixtures or as pure cis- or trans-isomers.

Asymmetric carbon atoms can possess the R-, S- or R,S-configuration.

Compounds of the general formula I are prepared according to known processes.

When X (in Y) in general formula I is a hydroxyl group, the compounds are preferably prepared by:

(a) reacting a carboxylic acid of the general formula:

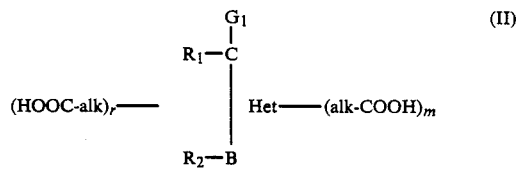

in which Het, B, R₁, R₂, alk, m and r have the above-given meanings, G₁ is a hydrogen atom or the grouping (alk-COOH)$_s$, whereby alk and s have the above-given meanings, with a mixture of phosphorous acid or phosphoric acid and a phosphorus halide and subsequently saponifying to the free diphosphonic acid, or (b) reacting a carboxylic acid chloride of the general formula:

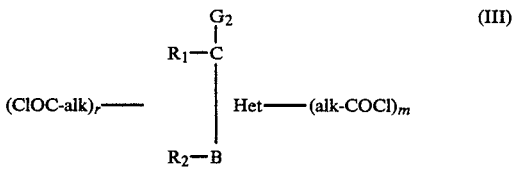
(III)

in which Het, R₁, R₂, alk, m and r have the above-given meanings, G₂ is a hydrogen atom or the grouping (alk-COCl)$_s$, with a trialkyl phosphite of the general formula:

P(OR')₃ (IV)

in which R' is a lower alkyl radical, to give an acyl phosphonate of the general formula:

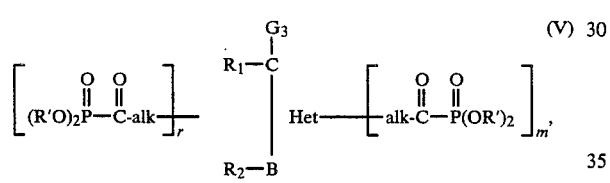
(V)

in which Het, B, R₁, R₂, R', alk, m and r have the above-given meanings, G₃ is a hydrogen atom or the grouping [alk-CO-P(O)(OR')₂]$_s$, whereby alk, R' and s have the above-given meanings, subsequently reacting with a dialkyl phosphite of the general formula:

(VI)

in which R' has the above-given meaning, to give a diphosphonate of the general formula:

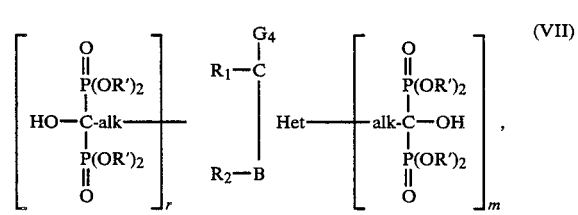
(VII)

in which Het, B, R₁, R₂, R', alk, m and r have the above-given meanings and G₄ is a hydrogen atom or the grouping [alk-C(OH)[P(O)(OR')₂]₂]$_s$, whereby alk, R' and s have the above-given meanings, and optionally saponifying the resultant tetraester to a diester or acid of general formula I, or (c) when X (in Y) in general formula I is an amino group optionally substituted by alkyl radicals, reacting a carboxylic acid derivative of the general formula:

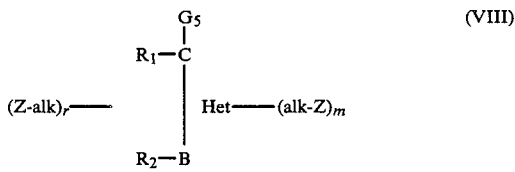
(VIII)

in which Het, B, R₁, R₂, alk, m and r have the above-given meanings, Z is a nitrile, imino ether or N,N-dialkylcarboxamido radical and G₅ is a hydrogen atom or the grouping (alk-Z)$_s$, whereby alk, Z and s have the above-given meanings, with a phosphorus compound of the general formula:

PT₃ (IX), in which T is a halogen atom, OH or OR', whereby R' has the above given meaning and possibly subsequently saponifying, or (d) when X in Y) in general formula I is a hydrogen atom, reacting a compound of the general formula:

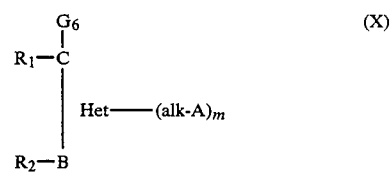
(X)

in which Het, B, R₁, R₂, alk, m and r have the above-given meanings, A is a reactive residue, for example a halogen atom or a sulphonate group, and G₆ is a hydrogen atom or the grouping (alk-A)$_s$, whereby alk, A and s have the above-given meanings, with a compound of the general formula:

(XI)

in which R' has the above-given meaning, to give a diphosphonate of the general formula:

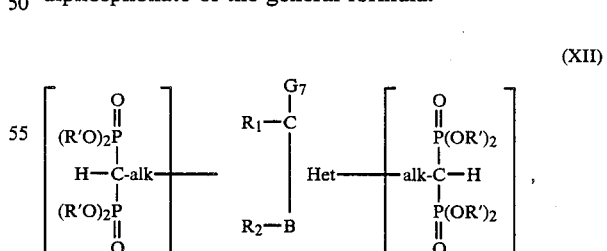
(XII)

in which Het, B, R₁, R₂, R', alk, m and r have the above-given meanings and G₇ is a hydrogen atom or the grouping [alk-CH[P(O)(OR')₂]₂]$_s$, whereby alk, R' and s have the above-given meanings, or (e) when Het in general formula I is a five- or six-membered ring, converting a compound of the general formula XIII

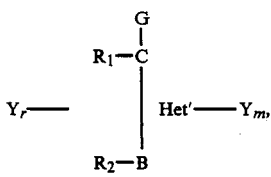

(XIII)

in which B, $R_1$, $R_2$, G, Y, m and r have the above-given meanings and Het' is a heteroaromatic five- or six-membered ring with one or two nitrogen atoms, by hydrogenation into a compound of general formula I, and optionally saponifying the resultant tetraester into a diester or acid of general formula I or, if desired, converting the compound obtained of formula I into a pharmacologically acceptable salt.

The carboxylic acids of general formula II used in process (a) are reacted with 1 to 2 and preferably 1.5 mole of phosphorous acid or phosphoric acid and 1 to 2 and preferably 1.5 mole of phosphorus trihalide at a temperature of 80° to 130° C. and preferably of 100° to 110° C. The reaction can also be carried out in the presence of a dilution agent, such as halogenated hydrocarbon, especially chlorobenzene or tetrachloroethane, or also dioxan. The subsequent hydrolysis can take place by boiling with water but preferably with semi-concentrated hydrochloric or hydrobromic acid.

In the case of process (b), the acid chloride of general formula III is reacted with the trialkyl phosphite of general formula IV at a temperature of 0° to 60° C. and preferably of 20° to 40° C. The reaction can be carried out without a solvent or also in the presence of an inert solvent, such as diethyl ether, tetrahydrofuran, dioxan or also a halogenated hydrocarbon, for example methylene chloride. The acyl phosphonate of general formula V resulting as intermediate can be isolated or further reacted directly.

The subsequent reaction is carried out in the presence of a weak base and preferably of a secondary amine, for example dibutylamine, at a temperature of 0° to 60° C. and preferably of 10° to 30° C.

In the case of process c), the nitriles of general formula VIII are reacted with phosphorous acid at a temperature of 110° to 180° C. The reaction can be carried out without or in the presence of an aprotic solvent, for example diglycol dimethyl ether or diglycol diethyl ether.

However, the nitriles can also be reacted with a phosphorus trihalide, for example phosphorus tribromide or phosphorus trichloride, in an inert solvent, for example dioxan or tetrahydrofuran, optionally with the addition of water, at a temperature of 20° to 80° C. Imino ethers of general formula VIII are preferably reacted with dialkyl phosphites in the presence of an equimolar amount of sodium in an inert solvent, for example diethyl ether, dioxan or also benzene, the reaction usually taking place at the reflux temperature of the solvent used. Acid amides of general formula VIII can be reacted in an inert solvent, for example a halogenated hydrocarbon or an ether, for example diethyl ether, with a mixture of phosphorus pentahalide/phosphorous acid or also of oxalyl chloride/trialkyl phosphite.

In the case of process d), the methylenediphosphonic acid ester of general formula XI is used in the form of its sodium or potassium salt. For this purpose, it is reacted with sodium, potassium or a corresponding hydride in an inert solvent, for example benzene, toluene or dimethylformamide, at a temperature of 0° to 40° C. and preferably at 25° C. The alkali metal salt is reacted, without isolation, with the appropriate halide or sulphonate. The temperature used is hereby 20° to 110° C.

In the case of process e), hydrogenation is carried out in the presence of a noble metal catalyst, for example palladium or platinum, preferably in acidic medium, for example, in aqueous solution, with or without the addition of an inorganic or organic acid at 1 to 100 bar and preferably 1 to 10 bar and at 20° to 80° C. and preferably at 20° to 50° C.

The tetraalkyl esters possibly obtained in the case of processes (b), (c), (d) and (e) can be saponified to diesters or free tetraacids. As a rule, the saponification to diesters takes place by treating the tetraalkyl esters with an alkali metal halide, preferably sodium iodide, in an appropriate solvent, for example acetone, at ambient temperature. There hereby results the symmetrical diester/disodium salt which can optionally be converted by an acidic ion exchanger into the diester/diacid. The saponification to free diphosphonic acids usually takes place by boiling with hydrochloric or hydrobromic acid. However, cleavage can also be carried out with a trimethylsilyl halide, preferably the bromide or iodide. On the other hand, the free diphosphonic acids can again be converted into the tetraalkyl esters by boiling with orthoformic acid alkyl esters. The free diphosphonic acids of general formula I can be isolated as free acids or in the form of their mono- or dialkali metal or ammonium salts. As a rule, the alkali metal salts can be well purified by reprecipitation from water/methanol or water/acetone.

The compounds of general formula I can, if desired, be subsequently converted into other compounds of general formula I. They can, for example, be alkylated or, by hydrogenolytic splitting off of an N-benzyl group, there can be prepared, for example, the corresponding unsubstituted compounds of general formula I.

As pharmacologically acceptable salts, there are especially used alkali metal and ammonium salts which are prepared in the usual way, for example by neutralisation of the compounds with inorganic or organic bases, for example sodium or potassium hydrogen carbonate, aqueous sodium hydroxide solution, aqueous potassium hydroxide solution, aqueous ammonia or amines, for example trimethyl or triethylamine.

The new compounds of general formula I according to the present invention and salts thereof can be administered enterally and parenterally in liquid or solid form. There are hereby used all conventional forms of administration, for example tablets, capsules, dragees, syrups, solutions, suspensions and the like. As injection medium, water is preferably used which contains the additives usual in the case of injection solutions, such as stabilising agents, solubilising agents and buffers.

Such additives include, for example, tartrate and citrate buffers, ethanol, complex formers (such as ethylene diamine-tetraacetic acid and non-toxic salts thereof) and high molecular weight polymers (such as liquid polyethylene oxide) for viscosity regulation. Liquid carrier materials for injection solutions must be sterile and are preferably filled into ampoules. Solid carrier materials include, for example, starch, lactose, mannitol, methyl cellulose, talc, highly dispersed silicic acids, higher molecular weight fatty acids (such as stearic acid), gelatine, agar-agar, calcium phosphate, magnesium stearate, animal and vegetable fats and solid high molecular weight polymers (such as polyethylene glycols); compositions suitable for oral administration can, if desired, contain flavouring and sweetening materials.

The dosaging can depend upon various factors, such as the manner of administration, species, age and/or individual state. The doses to be administered daily are about 1 to 1000 mg. and preferably 10 to 200 mg. in the case of humans and can be taken once or divided up several times.

Preferred according to the present invention are, apart from the compounds mentioned in the Examples and compounds derivable by combination of all the meanings of the substituents mentioned in the claims, the following diphosphonic acids, as well as their sodium salts and methyl and ethyl esters.

1-hydroxy-2-(octahydro-1-H-2-pyridin-3-yl)-ethane-1,1-diphosphonic acid, 1-hydroxy-1-(octahydro-1-H-2-pyridin-4-yl)-methane-1,1-diphosphonic acid,
2-(3,4-dihydroisoquinolin-1-yl)-ethane-1-hydroxy-1,1-diphosphonic acid,
1-hydroxy-2-(1,2,3,4-tetrahydroisoquinolin-1-yl)-ethane-1,1-diphosphonic acid,
1-hydroxy-2-(piperidin-2-yl)-propane-1,1-diphosphonic acid,
1-hydroxy-2-(1,2,3,4,5,6,7,8-octahydroisoquinolin-1-yl)-ethane-1,1-diphosphonic acid,
2-(decahydroisoquinolin-3-yl)-ethane-1-hydroxy-1,1-diphosphonic acid,
1-hydroxy-1-(1,2,3,4-tetrahydroisoquinolin-3-yl)-methane-1,1-diphosphonic acid,
1-hydroxy-1-(1,2,3,4-tetrahydroisoquinolin-4-yl)-methane-1,1-diphosphonic acid,
1-(decahydroisoquinolin-8-yl)-methane-1-hydroxy-1,1-diphosphonic acid
1-hydroxy-2-(1,2,3,4-tetrahydroisoquinolin-4-yl)-ethane-1,1-diphosphonic acid
1-(decahydroisoquinolin-3-yl)-methane-1-hydroxy-1,1-diphosphonic acid
1-(decahydroisoquinolin-4-yl)-methane-1-hydroxy-1,1-diphosphonic acid
2-(decahydroisoquinolin-4-yl)-ethane-1-hydroxy-1,1-diphosphonic acid
1-decahydroquinolin-8-yl)-methane-1-hydroxy-1,1-diphosphonic acid
2-(decahydroquinolin-2-yl)-ethane-1-hydroxy-1,1-diphosphonic acid
2-(decahydroquinolin-3-yl)-ethane-1-hydroxy-1,1-diphosphonic acid
2-(decahydroquinolin-8-yl)-ethane-1-hydroxy-1,1-diphosphonic acid
3-(decahydroquinolin-2-yl)-propane-1-hydroxy-1,1-diphosphonic acid
1-(decahydroquinolin-4-yl)-methane-1-hydroxy-1,1-diphosphonic acid
1-hydroxy-1-(octahydro-1-H-1-pyridin-3-yl)-methane-1,1-diphosphonic acid
1-decahydro-1-methylquinolin-3-yl)-methane-1-hydroxy-1,1-diphosphonic acid.
1-hydroxy-3-(1H-octahydroindol-2-yl)-propane-1,1-diphosphonic acid
1-hydroxy-1-(1H-octahydroindol-3-yl)-methane-1,1-diphosphonic acid
1-hydroxy-1-(1-propyloctahydroindol-3-yl)-methane-1,1-diphosphonic acid
1-hydroxy-2-(1H-octahydroindol-2-yl)-ethane-1,1-diphosphonic acid
1-hydroxy-2-(1-methyloctahydroindol-2-yl)-ethane-1,1-diphosphonic acid
1-hydroxy-2-(1H-octahydroindol-3-yl)-ethane-1,1-diphosphonic acid
1-hydroxy-1-(1H-octahydroindol-7-yl)-methane-1,1-diphosphonic acid
1-hydroxy-2-(1H-octahydroindol-7-yl)-ethane-1,1-diphosphonic acid
1-hydroxy-2-(2H-octahydroisoindol-1-yl)-ethane-1,1-diphosphonic acid
1-hydroxy-2-(pyrrolidin-2-yl)-ethane-1,1-diphosphonic acid
1-hydroxy-2-(1-methylpyrrolidin-2-yl)-ethane-1,1-diphosphonic acid
1-hydroxy-1-(octahydro-1-H-1-pyridin-4-yl)-methane-1,1-diphosphonic acid
1-hydroxy-2-(pyrrolidin-3-yl)-ethane-1,1-diphosphonic acid
1-hydroxy-2-(1-propylpyrrolidin-3-yl)-ethane-1,1-diphosphonic acid
3-(1-cyclohexylmethylpyrrolidin-2-yl)-propane-1-hydroxy-1,1-diphosphonic acid
1-hydroxy-1-(octahydro-1-H-1-pyridin-7-yl)-methane-1,1-diphosphonic acid
1-hydroxy-2-(octahydro-1-H-1-pyridin-2-yl)-ethane-1,1-diphosphonic acid
1-hydroxy-2-(tetrahydroquinoxalin-2-yl)-ethane-1,1-diphosphonic acid
1-hydroxy-3-(piperidin-2-yl)-butane-1,1-diphosphonic acid
1-hydroxy-5-(piperidin-2-yl)-pentane-1,1-diphosphonic acid
1-hydroxy-2-(piperidin-3-yl)-ethane-1,1-diphosphonic acid
1-hydroxy-3-(piperidin-3-yl)-butane-1,1-diphosphonic acid
2-(1H-hexahydroazepin-2-yl)-ethane-1-hydroxy-1,1-diphosphonic acid
1-(1H-hexahydroazepin-3-yl)-methane-1-hydroxy-1,1-diphosphonic acid
1-hydroxy-1-(3-pyrrolin-2-yl)-methane-1,1-diphosphonic acid
1-hydroxy-1-octahydroindolizin-8a-yl-methane-1,1-diphosphonic acid
1-hydroxy-1-[2,5,6,7-tetrahydro(3H)pyrrolizin-1-yl]-methane-1,1-diphosphonic acid
1-hydroxy-1-[5,6,7,7a-tetrahydro(3H)pyrrolizin-1-yl]-methane-1,1-diphosphonic acid
1-[hexahydro(3H)pyrrolizin-7a-yl]-methane-1-hydroxy-1,1-diphosphonic acid
2-[1,2-dihydro(3H)pyrrolizin-3-yl]-ethane-1-hydroxy-1,1-diphosphonic acid
2-[1,2-dihydro(3H)pyrrolizin-5-yl]-ethane-1-hydroxy-1,1-diphosphonic acid
2-[hexahydro(3H)pyrrolizin-7a-yl]-ethane-1-hydroxy-1,1-diphosphonic acid
1-hydroxy-2-(octahydro-1-H-2-pyridin-1-yl)-ethane-1,1-diphosphonic acid
1-[1,2-dihydro(3H)pyrrolizin-6-yl]-methane-1-hydroxy-1,1-diphosphonic acid
1-[1,2-dihydro(3H)pyrrolizin-7-yl]-methane-1-hydroxy-1,1-diphosphonic acid
1-hydroxy-1-[octahydro(4H)quinolizin-1-yl]-methane-1,1-diphosphonic acid
1-hydroxy-1-[octahydro(4H)quinolizin-2-yl]-methane-1,1-dihosphonic acid
1-[3,6,7,8,9,9a-hexahydro(4H)quinolizin-1-yl]-methane-1-hydroxy-1,1-diphosphonic acid 1-hydroxy-2-[octahydro(4H)quinolizin-1-yl]-ethane-1,1-diphosphonic acid 1-hydroxy-2-[octahydro(4H)quinolizin-2-yl]-ethane-1,1-diphosphonic acid The following Examples describe one of the process variants which can be used for the synthesis of the compounds according to the present invention but this is not to represent a limitation of the subject matter of the present invention. As a rule, the compounds are obtained as high melting solid products (mono- or disodium salt), the structure of which was verified by H, P and possibly by $^{13}C$ NMR spectroscopy. The purity of the substances was determined by means of C, H, N, P, S, Na analysis, as well as by thin layer electrophoresis (cellulose, oxalate buffer of pH=4.0). For the characterisation of the individual compounds, there are given the $M_{rel}$ values (=relative mobility), referred to pyrophosphate ($M_{rel}$=1).

EXAMPLE 1

1-1-(Decahydroquinolin-3-yl)-methane-1-hydroxy-1,1-diphosphonic acid 5.6 g. Decahydroquinoline-3-carboxylic acid (prepared by saponification of the corresponding ethyl ester which, in turn, was prepared by hydrogenation of ethyl 4-chloroquinoline-3-carboxylate with palladium on charcoal in glacial acetic acid at 5 bar and 60° C.) are suspended in 40 ml. chlorobenzene and mixed with 2.9 g. phosphorous acid. The reaction mixture is heated for 10 minutes to 120° C., then 3.8 ml. phosphorus trichloride are added dropwise and the mixture stirred for 8 hours at 120° C. After cooling, a yellow, amorphous mass is filtered off and washed with diethyl ether and the residue is heated for 5 hours under reflux with 60 ml. semi-concentrated hydrochloric acid. After cooling, the reaction mixture is filtered off with suction and the filtrate evaporated. The residue is dried and stirred with acetone. After 1 hour, the acetone is decanted off and the residue is dissolved in 16 ml. water and filtered. The filtrate is brought to a pH ≈5 with 2N aqueous sodium hydroxide solution and mixed with 150 ml. methanol. The precipitated product is filtered off with suction and dried. There are thus obtained 3.1 g. (26% of theory) of the disodium salt x 1 mole water; m.p. 270°–280° C., $M_{rel}$: 0.40.

In analogous way, there are obtained by the use of (a) 1-ethoxycarbonylpiperidin-2-ylacetic acid (m.p.: 58°–60° C.), 1-hydroxy-2-(piperidin-2-yl)-ethane-1,1-diphosphonic acid as monosodium salt x 1 mole water in a yield of 23% of theory; m.p.: 250°–255° C., $M_{rel}$: 0.40

(b) 1-methylpiperidin-2-ylacetic acid hydrochloride (m.p.: 178°–179° C.), 1-hydroxy-2-(1-methylpiperidin-2-yl)-ethane-1,1-diphosphonic acid as monosodium salt x 1 mole water in a yield of 28% of theory; m.p. 155°–160° C., $M_{rel}$: 0.40

(c) 3-(pyrrolidin-2-yl)-propionic acid (Can. J. Chem., 57, 1977), 1-hydroxy-3-(pyrrolidin-2-yl)-propane-1,1-diphosphonic acid as monosodium salt x 1 mole water in a yield of 39% of theory; m.p. 275°–280° C., $M_{rel}$: 0.50

(d) 1-benzylpyrrolidine-3-carboxylic acid (J. Chem.-Soc., 1959, 852), 1-(1-benzylpyrrolidin-3-yl)-methane-1-hydroxy-1,1-diphosphonic acid, the purification of which was carried out over an ion exchanger IR 120/H form; the compound was eluted with ammonia from the exchanger and obtained as an amorphous ammonium salt x 1 mole water in a yield of 12% of theory; $M_{rel}$: 0.40.

EXAMPLE 2

1-Hydroxy-3-(piperidin-2-yl)-propane-1,1-diphosphonic acid 1.5 g. 3-(Piperidin-2-yl)-propionic acid hydrochloride (m.p.: 193°–195° C., prepared by hydrogenation of 3-(2-pyridyl)-propionic acid in hydrochloric acid medium in the presence of platinum oxide) and 1.3 g. phosphorous acid are melted together at 80° C. After allowing to cool, 1.4 ml. phosphorus trichloride is added dropwise and further heated for 20 hours to 90° C. After cooling, 20 ml. water are carefully added thereto and heated under reflux for 7 hours. The cooled solution is treated with charcoal, filtered and the filtrate evaporated. After drying, the residue is stirred up several times with acetone, then taken up in water, the solution brought with 2N aqueous sodium hydroxide solution to a pH ≈5 and mixed with methanol. After stirring for some time with ice cooling, the precipitate is filtered off with suction and dried. There is obtained 1.05 g. (37% of theory) of the monosodium salt x 2 mole water; m.p. 270°–274° C.; $M_{rel}$: 0.41.

EXAMPLE 3

1-Hydroxy-1-(pyrrolidin-3-yl)-methane-1,1-diphosphonic acid 0.88 g. Ammonium salt of 1-(1-benzylpyrrolidin-3-yl)-methane-1,1-diphosphonic acid (see Example 1 e) is dissolved in 30 ml. water and hydrogenated in the presence of 0.7 g. palladium on charcoal at ambient temperature and normal pressure. After ending of the hydrogen take up, the catalyst is filtered off with suction, the filtrate is evaporated and the residue is treated with acetone. After suction filtration, there is obtained 0.44 g. (65% of theory) of the amorphous ammonium salt x 1 mole water, $M_{rel}$: 0.47.

EXAMPLE 4

1-Hydroxy-1-(4-piperidinyl)-methane-1,1-diphosphonic acid 12.9 g. Piperidine-4-carboxylic acid and 12.3 g. phosphorous acid are suspended in 130 ml. chlorobenzene, brought to 100° C. and mixed dropwise with 26.1 ml. phosphorus trichloride. The reaction is then continued at 130° C. After 25 hours, the chlorobenzene is distilled off and the residue is mixed with 170 ml. 6N hydrochloric acid and boiled for 13 hours. After filtering, the filtrate is concentrated and poured into 2 liters acetone. The greasy precipitate obtained becomes crystalline with isopropanol (7.7 g.=28% of theory). After recrystallisation from water, there are obtained 3.6 g. (13% of theory) as monohydrate of m.p. 238° C. sinters/24-6°–248° C. $M_{rel}$: 0.41.

(4a) In analogous way, from 3-(4-piperidinyl)-propionic acid (Biochem. J. 46, 192), there is obtained 1-hydroxy-3-(4-piperidinyl)-propane-1,1-diphosphonic acid as hydrochloride; yield 35% of theory; m.p. 230° C. sinters/234°–238° C. bubble formation (from aqueous methanol); $M_{rel}$: 0.40.

EXAMPLE 5

10 1-Hydroxy-3-(1,4,5 6-tetrahydropyrimidin-2-yl)-propane-1,1-diphosphonic acid

To 6 g. 3-(1,4,5,6-tetrahydropyrimidin-2-yl)propionic acid hydrochloride and 3.9 g. phosphorous acid, suspended in 60 ml. chlorobenzene, are added dropwise at 100° C. 8.3 ml. phosphorus trichloride and subsequently further stirred for 10 hours at the same temperature.

The chlorobenzene is then poured off, 120 ml. 6N hydrochloric acid are added thereto and boiled for 1 day. Subsequently, the hydrolysis solution is concentrated, poured into 600 ml. acetone and the separated oil brought to crystallisation with methanol. There are thus obtained 2.8 g. (29% of theory) of the desired diphosphonic acid ($M_{ref}$ 0.36) which is obtained as the monhydrate; m.p. 219°–226° C. (decomp.). The final purification takes place column chromatographically on Amberlite IR 120-H+.

The starting compound is obtained by hydrogenation, in the presence of palladium-charcoal, of the known 3-(2-pyrimidinyl)-acrylic acid, m.p. 214°–218° C., decomp. (JACS 72, 3541).

EXAMPLE 6

In a manner analogous to that described in Example 1, there are obtained by the reaction of phosphorous acid and phosphorus trichloride with (a) decahydroisoquinolin-1-ylacetic acid (m.p. 224°–229° C.; prepared by hydrogenation of 1,2,3,4,5,6,7,8-octahydroisoquinolin-1-ylacetic acid (synthesised according to Helv. Chim. Acta, 41, 129) in the presence of platinum oxide), 2-(decahydroisoquinolin-1-yl)-ethane-1-hydroxy-1,1-diphosphonic acid which, after purification over an ion exchanger IR 120/H form, was isolated as the free acid; yield 53% of theory; m.p. 219°–224° C. (decomp.); $M_{ref}$ 0.35

(b) octahydro(4H)quinolizine-3-carboxylic acid (m.p. 258°–261° C.; prepared by alkaline saponification of the ethyl ester which was synthesised according to Chem. Pharm. Bull., 27, 1454), 1-hydroxy-1-[octahydro(4H)quinolizin-3-yl]-methane-1,1-diphosphonic acid which was isolated as the disodium salt x 2 mole water in a yield of 22% theory; m.p. 285°–290° C. (decomp.); $M_{ref}$ 0.45.

(c) 1-methyl-1,2,3,4-tetrahydroquinoline-3-carboxylic acid (m.p. 90°–95° C.; preparation: ethyl 4-chloroquinoline-3-carboxylate is reacted with trimethyloxonium borofluorate to give the 1-methylquinolinium salt (m.p. 143°–146° C.); from this, by hydrogenation in the presence of platinum oxide, there is obtained ethyl 1-methyl-1,2,3,4-tetrahydroquinoline-3-carboxylate in the form of an oil which is then saponified under alkaline conditions to the corresponding acid), 1-hydroxy-1-(1-methyl-1,2,3,4-tetrahydroquinolin-3-yl)methane-1,1-diphosphonic acid which was isolated analogously to Example 1 e) as the ammonium salt; yield 25% of theory; m.p. 210°–220° C. (decomp.); $M_{ref}$ 0.40.

(d) 1-ethoxycarbonylpiperidine-3-carboxylic acid (oil; prepared by the reaction of piperidine-3-carboxylic acid hydrochloride with ethyl chloroformate at pH 9), 1-hydroxy-1-(piperidin-3-yl)-methane-1,1-diphosphonic acid which, after purification over an ion exchanger IR 120/H form, was isolated as the free acid x 1 mole water; yield 19% of theory. The hydrolysis with hydrochloric acid was hereby carried out over 10 hours in order to split off the carbethoxy group quantitatively; m.p. 260°–264° C. (decomp.); $M_{ref}$ 0.50

(e) 1-methylpiperidine-3-carboxylic acid hydrochloride (m.p. 166°–168° C.; preparation: methyl nicotinate is reacted with methyl iodide to give N-methyl-pyridinium iodide (m.p. 128°–130° C.), hydrogenated in the presence of platinum oxide to give methyl 1-methylpiperidine-3-carboxylate hydroiodide (m.p. 104°–105° C.) and subsequently, after alkaline saponification, isolated as the hydrochloride of the desired acid), 1-(1-methylpiperidin-3-yl)-methane-1-hydroxy-1,1-diphosphonic acid which, after purification over an ion exchanger IR 120/H form, was isolated as the free acid x 1 mole water; yield 18% of theory; m.p. 265°–270° C. (decomp.); $M_{ref}$ 0.50.

(f) hexahydro(3H)pyrrolizine-1-carboxylic acid (amorphous substance; prepared according to Arch. Pharm., 310, 179), 1-hexahydro(3)pyrrolizin-1-yl)-methane-1-hydroxy-1,1-diphosphonic acid as disodium salt x 2 mole water; yield 32% of theory; m.p. >300° C.; $M_{ref}$ 0.55.

(g) octahydro(4H)quinolizin-9a-ylacetic acid (amorphous substance; prepared by alkaline saponification of the ethyl ester which was synthesised according to Chem. Pharm. Bull., 23, 2387), 1-hydroxy-2-[octahydro(4H)-quinolizin-9a-yl]-ethane-1,1-diphosphonic acid which, after purification over an ion exchanger IR 120/H form, was isolated as the free acid x 1 mole water; yield 27% of theory; m.p. 200°–205° C.; $M_{ref}$ 0.45.

(h) 1,2-dihydro(3H)pyrrolizin-2-ylacetic acid (m.p. 65°–67° C.; prepared according to J. Org. Chem., 42, 3955), 1-[1,2-dihydro(3H)pyrrolizin-2-yl]-methane-1,1-diphosphonic acid as the disodium salt x 1 mole water; yield 19% of theory; m.p. >300° C.; $M_{ref}$ 0.55

(i) hexahydro(3H)pyrrolizin-2-ylacetic acid hydrochloride (m.p. 186°–188° C.; prepared by hydrogenation of the dihydro compound of Example 6 h) in the presence of platinum oxide as catalyst, 1-[hexahydro(3H)-pyrrolizin-2-yl]-methane-1-hydroxy-1,1-diphosphonic acid as the sodium salt x 1 mole water; yield 24% of theory; m.p. >300° C.; $M_{ref}$ 0.50.

TEST REPORT

Male Wistar rats from our own breeding weighing about 160 g were thyroparathyroidectcmized on day 1. On day 5, the success of the operation was controlled by measuring calcemia after a night fasting. From that day on, all the animals were group-fed, that means all of them ate the same quantity of food. Furthermore, the animals received then daily for 3 days 2 subcutaneous injections, on containing 25 μg of a synthetic retinoid, the other one the bisphonsphonate to be tested. Additionally, all animals were given 2 μg of thyroxine the first and last day of treatment 24 h after the last injection of the retinoid and the biphosphonate and after one night fasting, blood was taken by retroorbital puncture under ether anesthesia. Plasma calcium was then analyzed by means of atomic absorption.

The bisphosphonate were given first at a dose of 1 mg P/kg in a volume of 2 ml/kg. Thereupon, the compounds were given in a dose of 0,1 ; 0,01 and if high active in a dose of 0,001 mg P/kg.

TABLE

| Example | mg P/kg | | | |
| --- | --- | --- | --- | --- |
|  | 0.001 | 0.01 | 0.1 | 1 |
| 1b | (+) | +++ | +++ | +++ |
| 1c | (+) | +++ | +++ | +++ |
| 1d |  | 0 | + | +++ |
| 2 |  |  | + | +++ |

0 = Depression of Hypercalcaemie −0.99 to +0.99 mg %
(+) = Depression of Hypercalcaemie 1.0 to 1.99 mg %
+ = Depression of Hypercalcaemie 2.0 to 2.99 mg %
++ = Depression of Hypercalcaemie 3.0 to 3.99 mg %
+++ = Depression of Hypercalcaemie >4.0%

It will be understood that the specification and examples are illustrative but not limitative of the present invention and that other embodiments within the spirit and scope of the invention will suggest themselves to those skilled in the art.

What is claimed is:

1. A diphosphonic acid derivative of the formula:

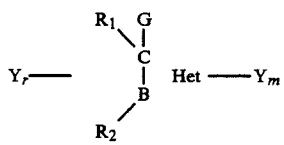 (I)

wherein Het is a piperidine ring wherein the nitrogen is unsubstituted or substituted by $C_1$–$C_4$ alkyl,
B is C-H,
$R_1$ and $R_2$ are each hydrogen,
Y is a group of the formula:

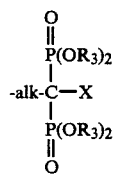

wherein $R_3$ is hydrogen or a $C_1$–$C_4$ alkyl, alk is a straight-chain or branched $C_1$–$C_6$ alkylene chain except that the chain cannot link with a heteroatom, X is hydrogen or a hydroxyl or amino group, G is hydrogen, m is 1 and r is 0, ; and the stereo-, cis- or trans-isomers and the pharmacologically acceptable salt thereof.

2. The compound of formula I of claim 1, wherein Het is a piperidine ring, B is C-H, $R_1$ and $R_2$ are hydrogen, Y is a group of the formula:

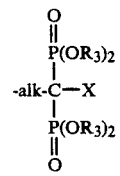

wherein $R_3$ is hydrogen or a $C_1$–$C_4$-alkyl, alk is a $C_1$–$C_2$-alkylene chain, X is hydroxyl, G is a hydrogen, r is 0 and m is 1.

3. The compound of claim 1 or 2 wherein the $C_1$–$C_4$ alkyl is methyl, ethyl or isopropyl.

4. The compound of claim 1 or 2 wherein when alk is an alkylene chain it is methylene, ethylene or propylene.

5. The compound of claim 1 designated 1-hydroxy-3-(piperidine-2-yl)-propane-1,1-diphosphonic acid and the physiologically active salt.

6. The compound of claim 1 designated 1-hydroxy-2-(piperidine-2-yl)-ethane-1,1-diphosphonic acid the physiologically active salt.

7. A pharmaceutical composition for the treatment or prophylaxis of calcium metabolism disturbance or disease wherein said composition contains a pharmaceutically effective amount of at least one compound of claim 1 or 2 in a pharmaceutically acceptable carrier.

8. A pharmaceutical composition for the treatment or prophylaxis of calcium disturbance or disease consisting of a pharmaceutically effective amount of at least one compound selected from the group consisting of 1-hydroxy-2-(1-methylpiperidine-2-yl)ethane-1,1-diphosphonic acid, 1-hydroxy-2-(piperidine-2-yl)-ethane-1,1-diphosphonic acid and 1-hydroxy-3-piperidine-2-yl)-propane-1,1-disphosphonic acid.

9. A method for the treatment of prophylaxis of calcium metabolism disturbance or disease comprising administering an effective amount of at least one of a pharmaceutically acceptable compound of claim 1 or 2.

10. The method of claim 7 wherein the daily dose is 1–1000 mg. in a human.

11. The method of claim 9 wherein the daily dose is 10–200 mg. in a human.

12. A method for the treatment or prophylaxis of calcium metabolism disturbance or disease comprising administering an effective amount of at least one of a pharmaceutically acceptable compound selected from the group consisting of 1-hydroxy-2-(1-methyl-piperidine-2-yl)-ethane-1, 1-diphosphonic acid, 1-hydroxy-2-(piperidine-2-yl)-ethane-1,1-diphosphonic acid, and 1-hydroxy-3-(piperidine-2-yl)-propane-1,1-diphosphonic acid.

13. The method of claim 12 wherein the daily dose is 1–1000 mg. in a human.

14. The method of claim 12 wherein the daily dose is 10–200 mg. in a human.

* * * * *

UNITED STATES PATENT AND TRADEMARK OFFICE
CERTIFICATE OF CORRECTION

PATENT NO. : 4,971,958
DATED : November 20, 1990
INVENTOR(S) : Bosies et al.

It is certified that error appears in the above-identified patent and that said Letters Patent is hereby corrected as shown below:

Col. 1, lines 50-53:   Formula (I) to read as follows:

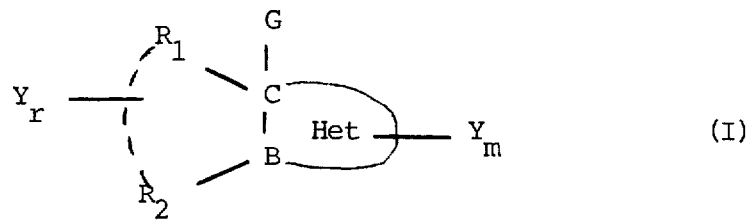

Col. 2, lines 64-66:   Formula (II) to read as follows:

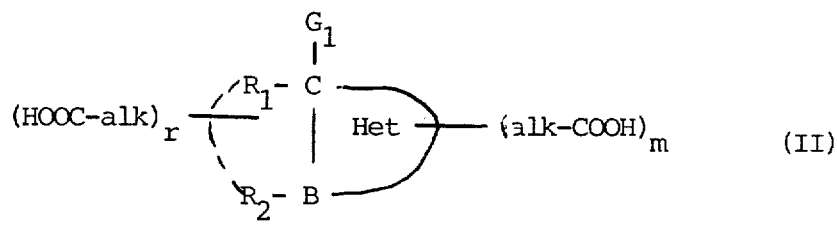

UNITED STATES PATENT AND TRADEMARK OFFICE
CERTIFICATE OF CORRECTION

PATENT NO. : 4,971,958
DATED : November 20, 1990
INVENTOR(S) : Bosies et al.

It is certified that error appears in the above-identified patent and that said Letters Patent is hereby corrected as shown below:

Col. 3, formula (III):   Formula (III) to read as follows:

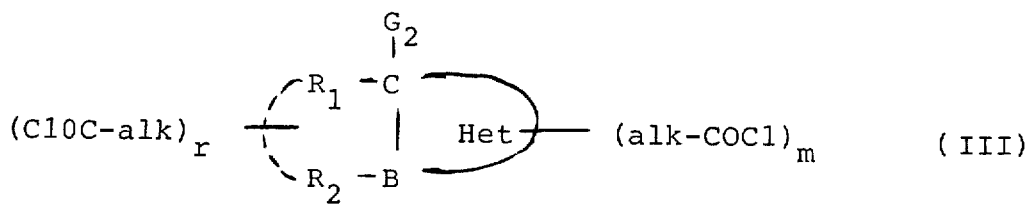

Col. 3, formula (V):   Formula (V) to read as follows:

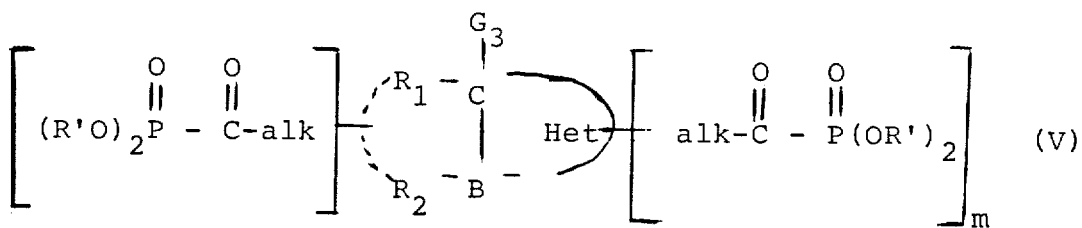

UNITED STATES PATENT AND TRADEMARK OFFICE
CERTIFICATE OF CORRECTION

PATENT NO. : 4,971,958
DATED : November 20, 1990
INVENTOR(S) : Bosies et al.

It is certified that error appears in the above-identified patent and that said Letters Patent is hereby corrected as shown below:

Col. 3, formula (VII):   Formula (VII) to read as follows:

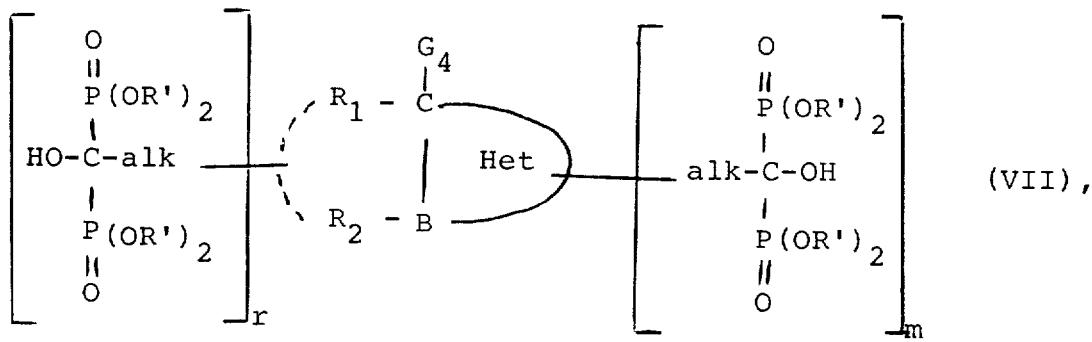

Col. 4, formula (VIII):   Formula (VIII) to read as follows:

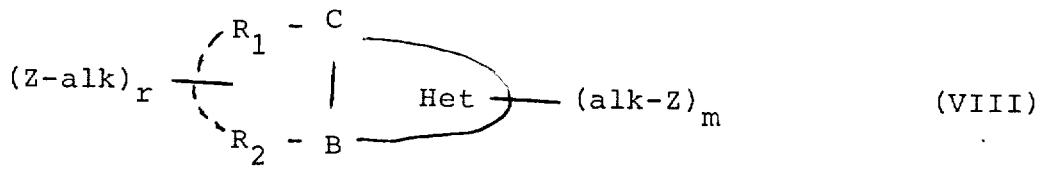

UNITED STATES PATENT AND TRADEMARK OFFICE
CERTIFICATE OF CORRECTION

PATENT NO. : 4,971,958

DATED : November 20, 1990

INVENTOR(S) : Bosies et al.

It is certified that error appears in the above-identified patent and that said Letters Patent is hereby corrected as shown below:

Col. 4, formula (X): Formula (X) to read as follows:

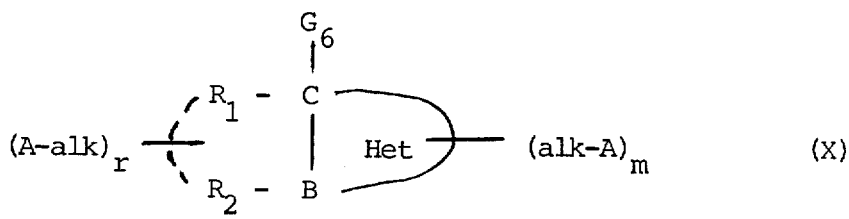

Col. 4, formula (XI): Formula (XI) to read as follows:

UNITED STATES PATENT AND TRADEMARK OFFICE
CERTIFICATE OF CORRECTION

PATENT NO. : 4,971,958

DATED : November 20, 1990

INVENTOR(S) : Bosies et al.

It is certified that error appears in the above-identified patent and that said Letters Patent is hereby corrected as shown below:

Col. 4, formula (XII):     Formula (XII) to read as follows:

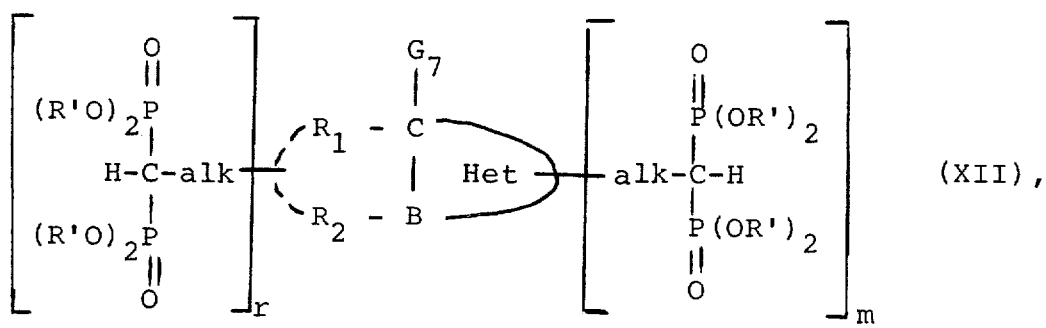

Col. 5, formula (XIII):    Formula (XIII) to read as follows:

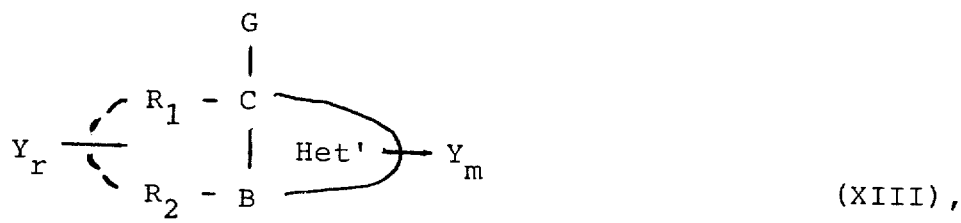

UNITED STATES PATENT AND TRADEMARK OFFICE
CERTIFICATE OF CORRECTION

PATENT NO. : 4,971,958

DATED : November 20, 1990

INVENTOR(S) : Bosies et al.

It is certified that error appears in the above-identified patent and that said Letters Patent is hereby corrected as shown below:

| | |
|---|---|
| Col. 9, line 21: | change "1-1-" to -- 1- --. |
| Col. 10, line 64: | delete "10". |
| Col. 12, line 38: | change "thyroparathyroidectcmized" to -- thyroparathyroidectomized --. |
| Col. 12, line 44: | change "on" to -- one --. |
| Col. 13, Claim 1, Formula I: | Formula (I) to read as follows: |

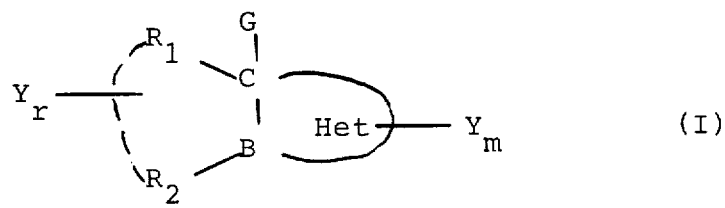

UNITED STATES PATENT AND TRADEMARK OFFICE
CERTIFICATE OF CORRECTION

PATENT NO. : 4,971,958
DATED : November 20, 1990
INVENTOR(S) : Bosies et al

It is certified that error appears in the above-indentified patent and that said Letters Patent is hereby corrected as shown below:

Col. 14, line 32
    Claim 10:               delete "7" and insert -- 9 --.

Signed and Sealed this

Eighth Day of June, 1993

Attest:

MICHAEL K. KIRK

*Attesting Officer*        *Acting Commissioner of Patents and Trademarks*